US010031056B2

(12) United States Patent
Bellin (10) Patent No.: US 10,031,056 B2
(45) Date of Patent: Jul. 24, 2018

(54) THERMOMECHANICAL TESTING OF SHEAR CUTTERS (71) Applicant: VAREL INTERNATIONAL IND., L.P., Carrollton, TX (US)

(72) Inventor: Federico Bellin, Tomball, TX (US)

(73) Assignee: VAREL INTERNATIONAL IND., L.P., Carrollton, TX (US)

( * ) Notice: Subject to any disclaimer, the term of this patent is extended or adjusted under 35 U.S.C. 154(b) by 218 days.

(21) Appl. No.: 15/198,645

(22) Filed: Jun. 30, 2016

(65) Prior Publication Data

US 2018/0003603 A1 Jan. 4, 2018

(51) Int. Cl.
*G01N 3/58* (2006.01)
*E21B 10/567* (2006.01)
*G01N 3/56* (2006.01)

(52) U.S. Cl.
CPC ............ *G01N 3/58* (2013.01); *E21B 10/567* (2013.01); *G01N 3/56* (2013.01); *G01N 2203/0053* (2013.01); *G01N 2203/0073* (2013.01); *G01N 2203/0224* (2013.01); *G01N 2203/0676* (2013.01)

(58) Field of Classification Search
None
See application file for complete search history.

(56) References Cited

U.S. PATENT DOCUMENTS

| 3,406,742 | A | * | 10/1968 | Naumann | G01N 3/32 165/267 |
|---|---|---|---|---|---|
| 4,346,754 | A | * | 8/1982 | Imig | G01N 3/02 165/254 |
| 5,833,021 | A | | 11/1998 | Mensa-Wilmot | |
| 6,003,623 | A | | 12/1999 | Miess | |
| 8,453,497 | B2 | | 6/2013 | Hall | |
| 8,974,357 | B2 | | 3/2015 | Kitayama | |
| 9,222,350 | B2 | | 12/2015 | Vaughn | |
| 2010/0199573 | A1 | | 8/2010 | Montross | |
| 2011/0148021 | A1 | | 6/2011 | Reese | |
| 2013/0067985 | A1 | | 3/2013 | Bellin | |
| 2013/0239652 | A1 | | 9/2013 | Pelfrene | |
| 2014/0250973 | A1 | | 9/2014 | Gledhill et al. | |
| 2015/0075252 | A1 | | 3/2015 | Bellin | |

OTHER PUBLICATIONS

European Search Report; European Patent Application No. 17177549.7-1553; dated Nov. 28, 2017.
Federico Bellin, Alfazazi Dourfaye, William King, and Mike Thigpen; "The Current State 15 of PDC Bit Technology Part 2 of 3: Leaching a Thin Layer at the Working Surface of a PDC Cutter to Remove the Cobalt Dramatically Reduces Diamond Degradation Due to Frictional Heat"; World Oil, Oct. 2010 issue, pp. 53-58; © 2010 by Gulf Publishing Company.

* cited by examiner

*Primary Examiner* — Jill Culler (57) ABSTRACT

A method for testing thermal fatigue resistance of a shear cutter includes: engaging the shear cutter with a rotating target cylinder; moving the shear cutter along the rotating target cylinder until the shear cutter is heated to a threshold temperature; cooling the shear cutter in response to heating of the shear cutter to the threshold temperature; and repeating the heating and cooling of the shear cutter.

12 Claims, 6 Drawing Sheets

| Specimen | # of Cycles until Failure |
|----------|---------------------------|
| A        | 5                         |
| B        | 8                         |
| C        | 10                        |

FIG. 6

THERMOMECHANICAL TESTING OF SHEAR CUTTERS

BACKGROUND OF THE DISCLOSURE

Field of the Disclosure

The present disclosure generally relates to thermomechanical testing of shear cutters.

Description of the Related Art

U.S. Pat. No. 8,453,497 discloses a fixture for holding a cutter for a vertical turret lathe including a block with a blind hole. A cutter with an indenter on its distal end may be secured within the hole such that a portion of the indenter comprises a positive rake angle. A method for testing cutters may comprise securing a cutter on a fixture of a vertical turret lathe which has a cutting material positioned adjacent the cutter. The cutting material may be rotated around a rotational axis at a constant rotational velocity. The fixture may be urged laterally such that the cutter progressively moves towards a periphery of the cutting material. The rotational velocity may be decreased as the cutter moves laterally to maintain a relative constant linear velocity between the cutting material and the cutter.

U.S. Pat. No. 9,222,350 discloses a cutting element for an earth-boring drilling tool and its method of making. The cutting element may include a substrate, a superhard layer, and a sensing element. The superhard layer may be bonded to the substrate along an interface. The superhard layer may have a working surface opposite the interface and an outer peripheral surface. The outer peripheral surface may extend between the working surface and the interface. The sensing element may comprise at least a part of the superhard layer.

U.S. Pat. App. Pub. No. 2011/0148021 discloses a target cylinder and a method for fabricating the target cylinder. The target cylinder includes a first end, a second end, and a sidewall extending from the first end to the second end. At least one of the second end and the sidewall is an exposed portion that makes contact with a superhard component to determine at least one property of the superhard component. The exposed portion comprises at least one soft material and at least one hard material that is interveningly positioned between or within the soft material in a predetermined and repeatable pattern. In one embodiment, the differential of the unconfined compressive strength between the hard material and the soft material ranges from about 1,000 psi to about 60,000 psi.

U.S. Pat. App. Pub. No. 2013/0067985 discloses a method and apparatus for testing the abrasive wear resistance of PDC cutters or other superhard materials. The method includes obtaining a first cutter having a first substrate and a first cutting table coupled thereto and obtaining a second cutter having a second substrate and a second cutting table coupled thereto. The method also includes positioning a surface of the first cutting table in contact with a surface of the second cutting table. The method also includes rotating at least one of the first cutters and the second cutters where at least a portion of the first and/or second cutting tables is removed. The method includes determining the amount of first and/or second cutting table removed. The apparatus includes a first holder coupled to the first cutter and a second holder coupled to the second cutter, where at least one holder rotates circumferentially.

U.S. Pat. App. Pub. No. 2013/0239652 discloses a target cylinder, a method for testing a superhard component thereon, and a method for selecting an untested component for use in field applications. The target cylinder includes a first end, a second end, and a side wall extending from the first end to the second end. At least one of the second end and the sidewall is an exposed portion that makes contact with the superhard component to determine at least one property of the superhard component. The target cylinder is formed from a first material evenly distributed throughout a second material. Upon testing superhard components at one or more impact frequencies, untested superhard components are selected based upon field anticipated impact frequencies.

U.S. Pat. App. Pub. No. 2014/0250973 discloses a system and a method of testing a superabrasive cutter. The system of testing a superabrasive cutter may include a spinning wheel holding the superabrasive cutter; a rock feeding into a rotation of the superabrasive cutter on the spinning wheel; and a plurality of sensors operably attaching to the spinning wheel and the rock to detect properties of the superabrasive cutter. The method of testing a superabrasive cutter may include steps of attaching a superabrasive cutter to a spinning wheel; moving a rock into a rotation of the superabrasive cutter on the spinning wheel; and communicably coupling a first sensor to the superabrasive cutter.

U.S. Pat. App. Pub. No. 2015/0075252 discloses methods and techniques for determining wear abrasion resistance of superhard components, such as cutters used in down-hole drilling tools. The methods and techniques produce an efficiency ratio of a superhard component through data obtained from a vertical turret lathe test. The efficiency ratio is the ratio between the volume of a target cylinder removed by the superhard component during the vertical turret lathe test and the normal force applied onto the superhard component by the target cylinder. The efficiency ratio is indicative of the energy efficiency of the superhard component.

SUMMARY OF THE DISCLOSURE

The present disclosure generally relates to thermomechanical testing of shear cutters. In one embodiment, a method for testing thermal fatigue resistance of a shear cutter includes: engaging the shear cutter with a rotating target cylinder; moving the shear cutter along the rotating target cylinder until the shear cutter is heated to a threshold temperature; cooling the shear cutter in response to heating of the shear cutter to the threshold temperature; and repeating the heating and cooling of the shear cutter.

In another embodiment, a method for testing thermal fatigue resistance of a shear cutter includes: engaging the shear cutter with a rotating target cylinder; moving the shear cutter along the rotating target cylinder without coolant, thereby heating the shear cutter; cooling the shear cutter after heating the shear cutter for a period of time; and repeating the heating and cooling of the shear cutter.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

Figure 1:
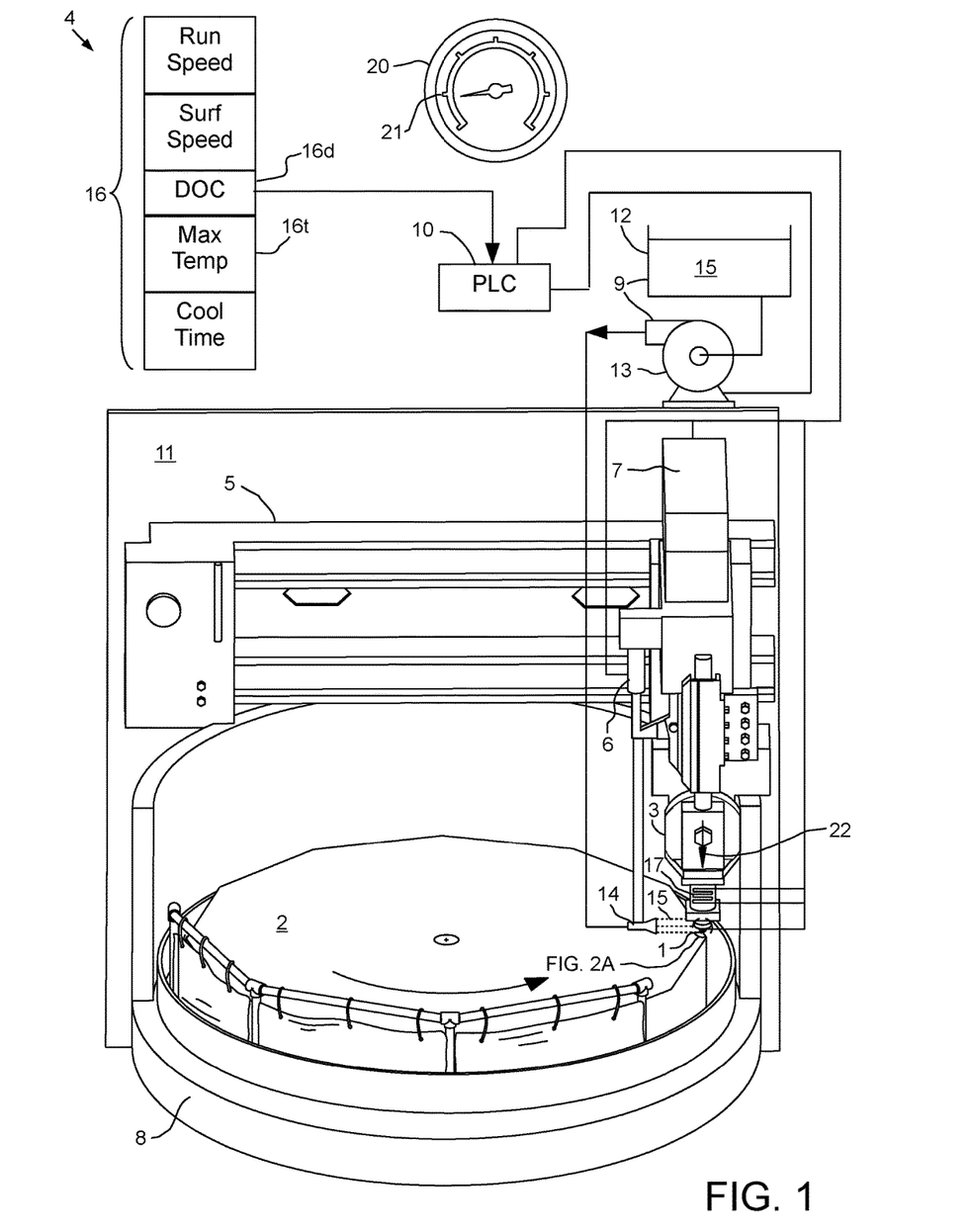
FIG. 1 illustrates commencement of a thermomechanical vertical turret lathe (VTL) test by engagement of a shear cutter with a target cylinder, according to one embodiment of the present disclosure.

FIG. 1 illustrates commencement of a thermomechanical vertical turret lathe (VTL) test by engagement of a shear cutter 1 with a target cylinder 2, according to one embodiment of the present disclosure. To prepare for commencement of the test, the shear cutter 1 may be mounted to a head 3 of the VTL 4. The VTL 4 may include the head 3, a track 5, a plunger 6, a runner 7, a turntable 8, a cooling system 9, a programmable logic controller (PLC) 10, and a frame 11.

The track 5 and turntable 8 may be mounted to the frame 11. The runner 7 may be transversely movable along the track 5 by operation of a track actuator (not shown), such as a rack and pinion. The rack may extend along the track 5 and the pinion motor may be mounted to the runner 7. The pinion motor may be operated by the PLC 10 via a control line. The plunger 6 may be a piston and cylinder assembly having an upper end connected to the runner 7 and a lower end connected to the head 3. The plunger 6 may be operated by the PLC via a control line to raise and lower the head 3 relative to the turntable 8. Each of the track actuator and the plunger 6 may also include a position sensor in communication with the PLC 10. The target cylinder 2 may be mounted on the turntable 8. The turntable 8 may include a motor (not shown) for rotating the target cylinder 2 relative to the head 3. The turntable 8 may also include a tachometer (not shown) in communication with the PLC 10. The target cylinder 2 may be made from hard natural rock, such as granite, marble, or sandstone.

Alternatively, the target cylinder 2 may be a synthetic composite having a matrix of concrete and plates of hard natural rock or synthetic ceramic disposed about the matrix in a pattern. The concrete may include cement, such as Portland cement, reinforced with quartzite sand. Alternatively, the rock or ceramic may be dispersed throughout the cement as large particles.

The cooling system 9 may include a reservoir 12, a pump 13, a nozzle 14, and a plurality of fluid conduits. The reservoir 12 and pump 13 may be mounted to the frame 11 and the nozzle 14 may be mounted to the head 3 or the plunger 6. A supply conduit may connect the reservoir 12 to an inlet of the pump 13 and a discharge conduit may connect an outlet of the pump to the nozzle 14. The discharge conduit may be flexible, such as a hose, to accommodate movement of the head 3 relative to the runner 7 and movement of the runner 7 relative to the frame 11. A quantity of coolant 15 may be disposed in the reservoir 12. The coolant 15 may be a liquid, such as water. The nozzle 14 may be disposed in proximity to the mounted shear cutter 1 and aimed thereat to spray coolant 15 onto the shear cutter 1. The PLC 10 may be in communication with the pump 13 via a control line for selectively activating and deactivating the pump.

Alternatively, the nozzle 14 may be mounted to the frame 11. Alternatively, the nozzle 14 may be aimed to spray the coolant onto the target cylinder 2 instead of onto the shear cutter 1, thereby indirectly cooling the shear cutter 1. Alternatively, the reservoir 12 may be omitted, the coolant 15 may be air instead of water, and the cooling system 9 may include a compressor instead of the pump 13. Alternatively, the coolant 15 may be oil and the turntable 8 may have a sump and a recycle pump for returning the oil to the reservoir 12.

Also in preparation for commencement of the test, one or more parameters 16 may be input to the PLC 10. The parameters 16 may include depth of cut (DOC) 16$d$, a temperature threshold (Max Temp) 16$t$, and/or cooling time (Cool Time). Additional parameters may include a surface speed (Surf Speed) the turntable 8 and/or a speed of the runner 7 (Run Speed). The threshold temperature 16$t$ may range between eight hundred and thirteen hundred degrees Celsius. During testing, the PLC 10 may utilize measurements from the position sensor of the track actuator and may adjust an angular speed of the turntable motor so that the target cylinder rotates at a constant surface speed relative to the shear cutter. The surface speed may range between three hundred and six hundred fifty feet per minute (ninety-one and one hundred ninety-eight meters per minute).

Figure 2A:
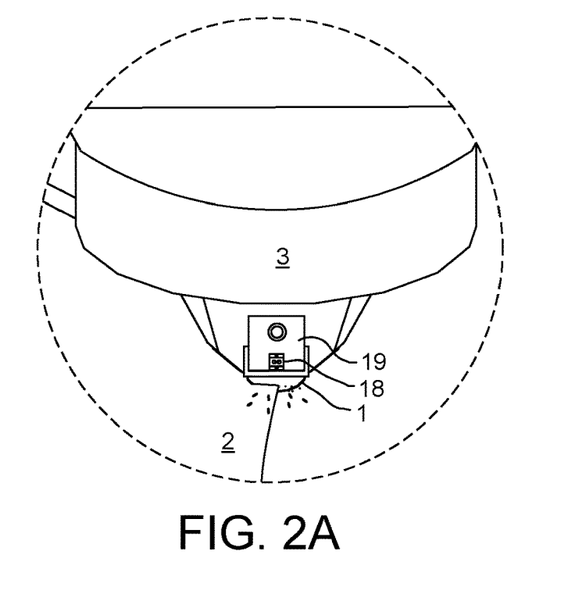
FIG. 2A is an enlargement of a portion of FIG. 1.
Figure 2B:
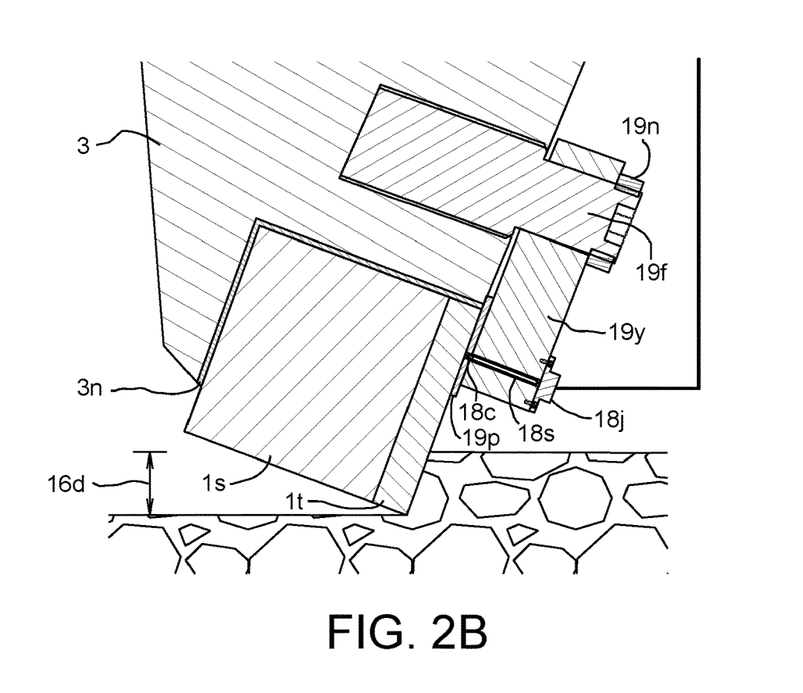
FIG. 2B illustrates engagement of the shear cutter with the target cylinder.

FIG. 2A is an enlargement of a portion of FIG. 1. FIG. 2B illustrates engagement of the shear cutter 1 with the target cylinder 2. Referring also to FIG. 1, the head 3 may include one or more sensors in communication with the PLC 10 via a data cable for monitoring the test. The PLC 10 may include a memory unit (not shown) for recording measurements from the sensors and a cycle count. The sensors may include a load cell 17 and a thermometer, such as a thermocouple 18. The load cell 17 may be mounted to the head 3 for measuring force 22 exerted by the plunger 6 onto the shear cutter 1 and/or reaction force (not shown) exerted by the target cylinder 2 onto the shear cutter. The shear cutter 1 may be mounted to a pocket formed in the head 3, such as by a clamp 19. The pocket may be lined with a thermally insulating material 3$n$, such as a ceramic, such as alumina. The thermally insulating material 3$n$ may obstruct heat transfer from the shear cutter 1 to the head 3 during a heating cycle of the test. The pocket may be configured such that the cutter 1 engages the target cylinder 2 at a positive back rake angle.

The shear cutter 1 may include a cutting table 1$t$ attached to a cylindrical substrate 1$s$. The cutting table 1$t$ may be circular and the substrate 1$s$ may be a circular cylinder. The cutting table 1$t$ may be made from a superhard material, such as polycrystalline diamond (PCD), attached to a hard substrate, such as a cermet, thereby forming a compact, such as a polycrystalline diamond compact (PDC). The cermet may be a cemented carbide, such a group VIIIB metal-carbide, such as cobalt-tungsten carbide. The cutting table 1$t$ may have an interface with the substrate 1$s$ and a cutting face opposite to the interface. The cutting table 1$t$ may be non-treated or thermally stable.

Alternatively, the shear cutter 1 may be oval. Alternatively, the superhard material may be cubic boron nitride or impregnated diamond.

The clamp 19 may include a threaded fastener 19$f$ screwed into the head 3, a yoke 19$y$ disposed onto the fastener, and a nut 19$n$ for securing the yoke onto the fastener. The clamp 19 may further include a pad 19$p$ disposed between the yoke 19$y$ and the shear cutter 1 for evenly distributing a clamping force along the cutting table it. The pad 19$p$ may be made from a thermally insulating material to obstruct heat transfer from the shear cutter 1 to the yoke 19$y$ during the heating cycle.

The thermocouple 18 may include a contact 18c, a pair of sensing wires 18s, a junction 18j, and a pair of lead wires arranged together in a cable. The contact 18c may be mounted to the pad 19p, such as by soldering, brazing, or interference fit therein. As the nut 19n is being screwed onto the fastener 19f, the yoke 19y may be advanced toward the cutting table 1t until the contact 18c is pressed firmly into thermal engagement with the cutting table. A first end of the sensing wires 18s may be secured to the contact 18c and the sensing wires may extend through an opening formed in the pad 19p and a passage formed in the yoke 19y. The junction 18j may be mounted on a surface of the yoke opposite to the cutting table it, such as by one or more fasteners. The junction 18j may connect each second end of the sensing wires 18s to an end of a respective lead wire. The thermocouple 18 may further include a reference temperature sensor (not shown) disposed in the junction 18j and a reference wire may also be arranged in the cable with the lead wires. The cable may extend to the PLC 10.

Alternatively, the contact 18c may be mounted to a surface of the yoke 19y facing the cutting table 1t, such as by soldering or brazing, and the contact may extend through an opening formed in the pad 19p. Alternatively, the shear cutter 1 may be brazed into the pocket and the contact 18c may be brazed or soldered onto the cutting table 1t. Alternatively, the contact 18c may be mounted to the substrate 1s instead of the cutting table 1c.

Once the preparations have been completed, the test may begin. The turntable 8 may be activated to rotate the target cylinder 2. The PLC 10 may operate the track actuator to position the shear cutter 1 into alignment with an outer surface of the target cylinder 2. The PLC 10 may then activate the pump 13 so that coolant 15 is sprayed onto the shear cutter 1. The PLC 10 may then operate the plunger 6 to lower the head 3 until the shear cutter 1 engages the outer surface of the target cylinder 2. The PLC 10 may continue to operate the plunger 6 to press the shear cutter into the target cylinder until the DOC 16d is reached.

Figure 3:
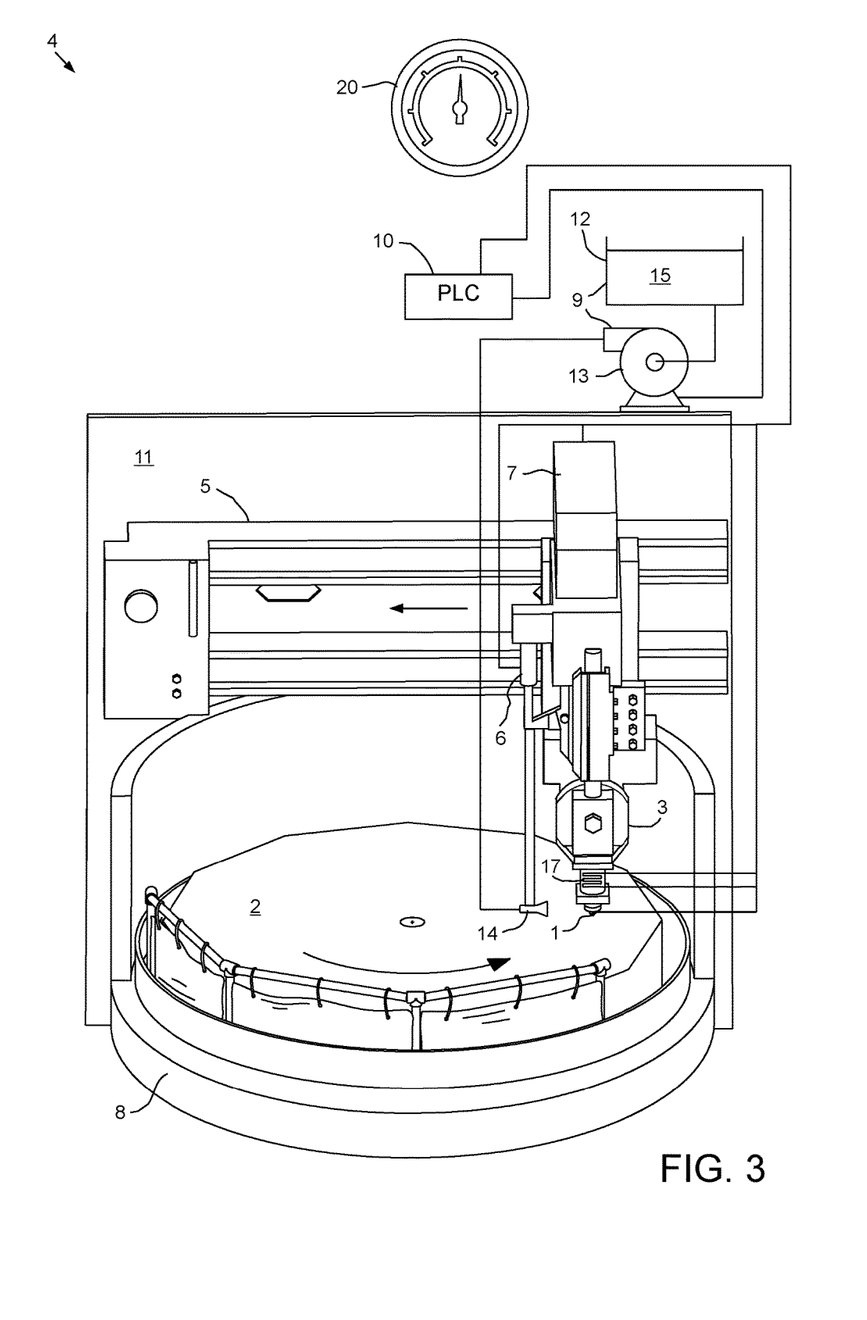
FIG. 3 illustrates a heating cycle of the test.

FIG. 3 illustrates a heating cycle of the test. Once the shear cutter 1 has penetrated the target cylinder to the DOC 16d, the PLC 10 may lock the plunger 6 and may deactivate the pump 13, thereby halting the flow of coolant 15 and beginning the heating cycle. The PLC 10 may then operate the track actuator to move the head 3 and mounted shear cutter 1 radially inward along a top of the target cylinder 2 as the target cylinder rotates relative thereto. The cutter 1 may shear material from the target cylinder 2 and heat may be generated by the cutting, thereby increasing a temperature 20 of the cutting table 1t.

Figure 4:
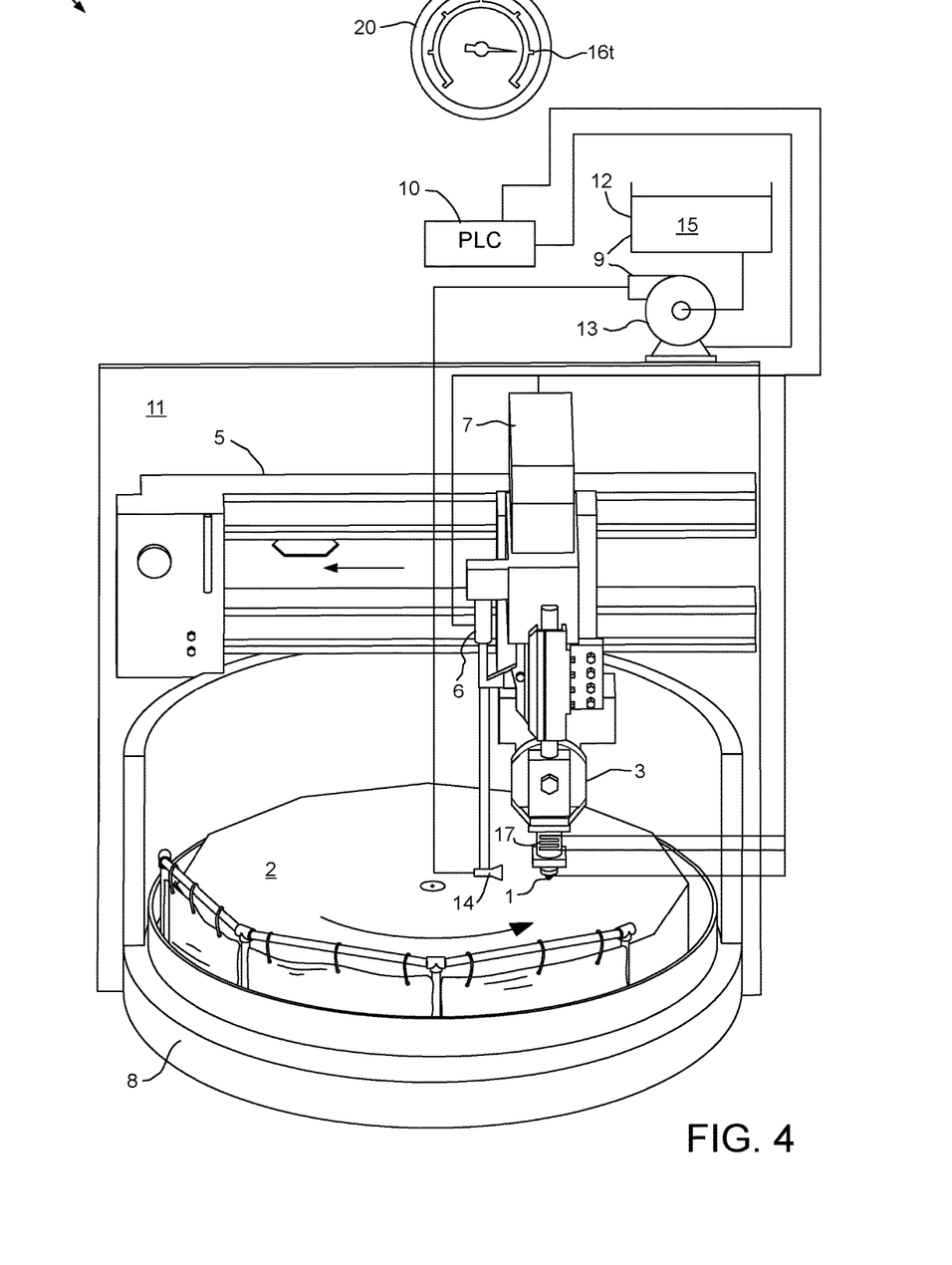
FIG. 4 illustrates the end of the heating cycle.

FIG. 4 illustrates the end of the heating cycle. During the heating cycle, the PLC 10 may monitor the thermocouple 18 and compare the measured temperature 20 to the threshold temperature at a sampling frequency, such as once per second. The heating cycle may continue until the temperature 20 increases to the threshold temperature 16t. The PLC 10 may record the temperature measurements in the memory unit. The PLC 10 may also sample measurements from the load cell 17 and record these measurements in the memory unit at the sampling frequency.

Figure 5:
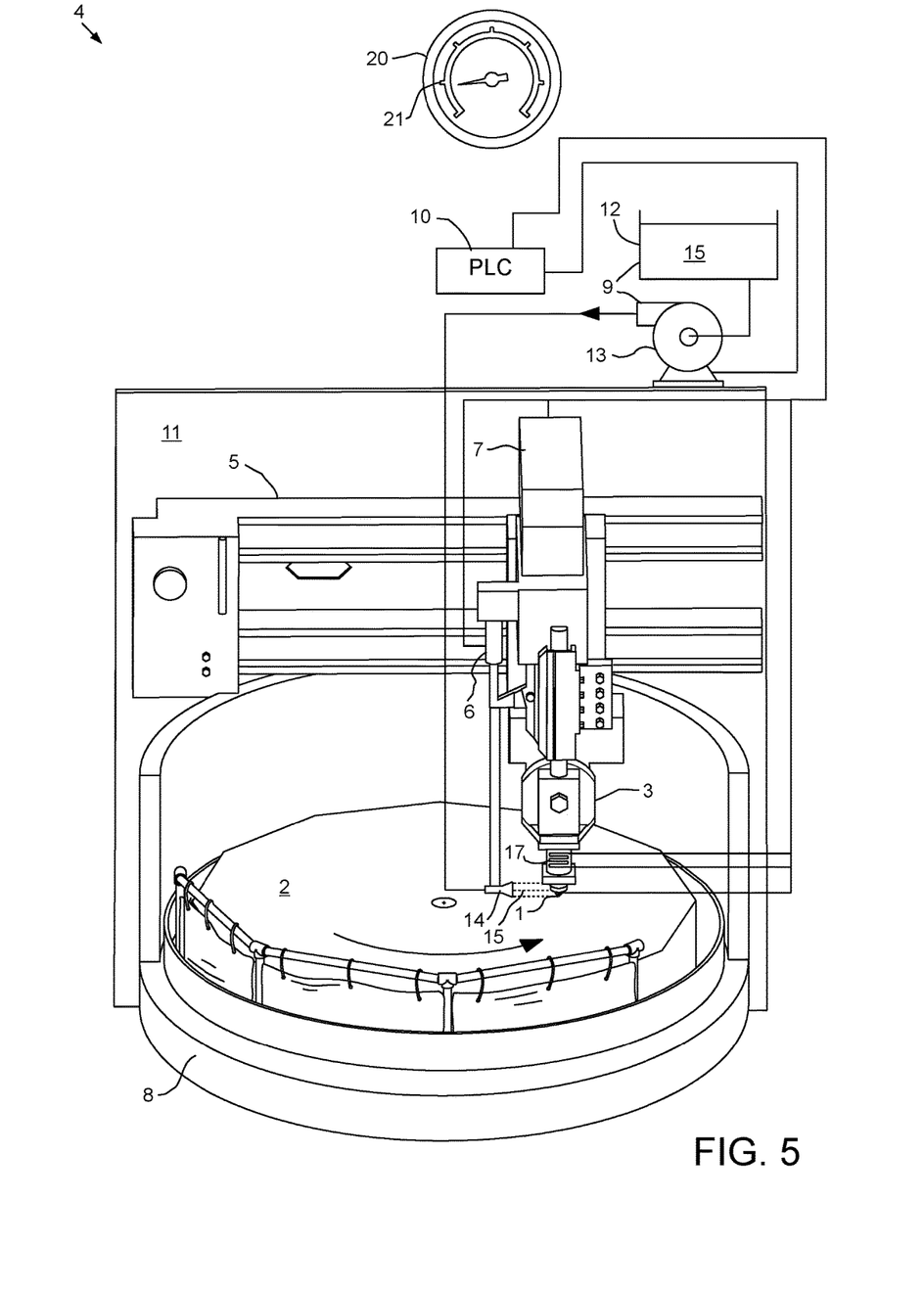
FIG. 5 illustrates a cooling cycle of the test.

FIG. 5 illustrates a cooling cycle of the test. Once the PLC 10 detects that the threshold temperature 16t has been reached, the PLC may reactivate the pump 13, thereby spraying the coolant 15 onto the hot shear cutter 1. The PLC 10 may operate the pump 13 for a period of time equal to the cooling time and then the PLC may deactivate the pump. The cooling time may be selected to quench the hot shear cutter 1 to a cold temperature 21, such as less than or equal to one-half, one-third, one-fourth, or one-eighth of the threshold temperature 16t. The PLC 10 may also sample temperature and load cell measurements and record the measurements in the memory unit at the sampling frequency during the cooling cycle. The cutter 1 may remain in engagement with the target cylinder 2 during the cooling cycle. The PLC 10 may halt operation of the track actuator to facilitate cooling.

Alternatively, the cold temperature 21 may be input to the PLC 10 instead of the cooling time and the PLC 10 may utilize the thermocouple 18 to determine when to terminate the cooling cycle. Alternatively, the pump 13 may be operated during the heating cycle but at a reduced flow rate relative to the cooling cycle. Alternatively, a heating time may be input to the PLC 10 instead of a threshold temperature and the heating cycle may be performed for the heating time regardless of the cutter temperature. Alternatively, the PLC 10 may maintain operation of the track actuator during the cooling cycle.

Once the shear cutter 1 has reached the inner periphery of the target cylinder 2, the PLC 10 may operate the plunger 6 to raise the head 3 and the cutter 1 from the target cylinder 2, move the head and cutter back into alignment with the outer surface of the target cylinder, and operate the plunger to lower the head and cutter into engagement with the target cylinder and further advance the cutter into the target cylinder by the DOC 16d.

Alternatively once the shear cutter 1 has reached the inner periphery of the target cylinder 2, the PLC 10 may halt the track actuator, unlock the plunger 6, and operate the plunger to further advance the cutter into the target cylinder by the DOC 16d. The PLC 10 may then reverse operation of the track actuator to move the shear cutter 1 radially inward along the target cylinder 2.

Figure 6:
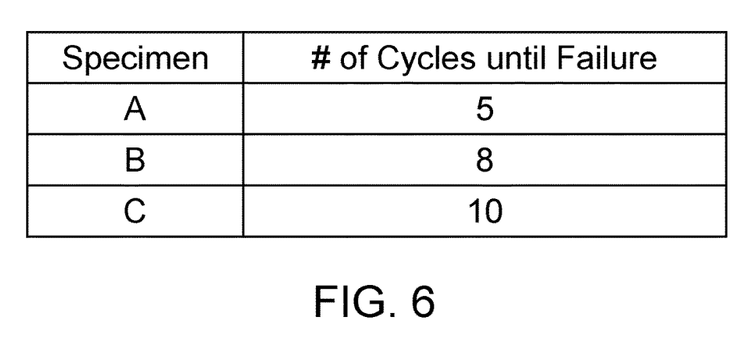
FIG. 6 illustrates results of tests performed on a plurality of shear cutters.

FIG. 6 illustrates results of tests performed on a plurality of shear cutters. Once the cooling cycle has completed, the heating and cooling cycles may be repeated until the cutter 1 fails. Cutter failure may be detected by the PLC 10 monitoring the load cell measurements during the test. A rapid decrease in the load cell measurements may indicate fracture of the cutting table 1t. Once failure of the cutting table 1t has been detected, the PLC 10 may record the number of test cycles endured by the shear cutter 1 and terminate the test. One test cycle may include one heating cycle and one cooling cycle. The test may be performed on other types of cutters and the test results may be used to compare the types of cutters for selection to install the optimum type on a drill bit. The type of cutters enduring the most number of test cycles may be deemed to have the greatest thermal fatigue resistance.

Alternatively, a plurality of cutters from each type may be tested and an average from each type may be used to compare the different types. Alternatively, the test may be performed on cutters of the same or similar type but from different batches to ensure quality.

Advantageously, the present invention may more accurately simulate drilling than the prior art discussed above due to thermal fatigue exerted on a drill bit by drilling stoppages to add joints/stands of drill pipe to the drill string.

While the foregoing is directed to embodiments of the present disclosure, other and further embodiments of the disclosure may be devised without departing from the basic scope thereof, and the scope of the invention is determined by the claims that follow.

The invention claimed is:

1. A method for testing thermal fatigue resistance of a shear cutter, comprising:
    engaging the shear cutter with a rotating target cylinder;
    moving the shear cutter along the rotating target cylinder until the shear cutter is heated to a threshold temperature;

cooling the shear cutter in response to heating of the shear cutter to the threshold temperature; and repeating the heating and cooling of the shear cutter, wherein:

the threshold temperature ranges between eight hundred and thirteen hundred degrees Celsius, the shear cutter is cooled to a cold temperature, and the cold temperature is less than or equal to one half of the threshold temperature the shear cutter is cooled by spraying liquid coolant onto the shear cutter at a cooling flow rate, and the shear cutter is heated without spraying the liquid coolant onto the shear cutter or spraying the liquid coolant onto the shear cutter at a reduced flow rate relative to the cooling flow rate.

2. The method of claim 1, wherein:

the heating and cooling of the shear cutter are repeated until the shear cutter fails, and the method further comprises counting a number of test cycles that the shear cutter endured.

3. The method of claim 2, further comprising:

repeating the method for a second cutter; and comparing the number of test cycles of the shear cutter to the number of test cycles of the second cutter.

4. The method of claim 1, wherein the threshold temperature is detected by a thermocouple engaged with the shear cutter.

5. The method of claim 4, wherein the thermocouple is engaged with a cutting table of the cutter.

6. The method of claim 5, wherein the method is performed using a vertical turret lathe.

7. The method of claim 6, wherein:

the shear cutter is clamped to a head of the vertical turret lathe, and a contact of the thermocouple is disposed between the clamp and the shear cutter.

8. The method of claim 1, wherein the shear cutter is heated without any coolant.

9. The method of claim 1, wherein:

the shear cutter is cooled by spraying liquid coolant onto the shear cutter, and the coolant is sprayed for a preset period of time.

10. The method of claim 1, wherein the cutter is a polycrystalline diamond compact cutter.

11. The method of claim 1, further comprising measuring a force exerted on the shear cutter during heating and cooling.

12. The method of claim 11, wherein:

the heating and cooling of the shear cutter are repeated until the shear cutter fails, and the measured force is used to detect failure of the shear cutter.

* * * * *